United States Patent [19]

Lund et al.

[11] Patent Number: 5,006,662
[45] Date of Patent: Apr. 9, 1991

[54] MANUFACTURING PROCESS FOR A NAPHTHOTRIAZOLE STILBENE FLUORESCENT AGENT

[75] Inventors: Richard B. Lund, Jackson; Glenn W. Brown, Wagarville, both of Ala.

[73] Assignee: Ciba-Geigy Corp., Ardsley, N.Y.

[21] Appl. No.: 423,721

[22] Filed: Oct. 19, 1989

Related U.S. Application Data

[63] Continuation of Ser. No. 259,506, Oct. 17, 1988, abandoned, which is a continuation of Ser. No. 33,382, Apr. 2, 1987, abandoned.

[51] Int. Cl.$^5$ ............................................. C07D 249/24
[52] U.S. Cl. ...................................................... 548/260
[58] Field of Search ......................... 548/257, 261, 260

[56] References Cited

U.S. PATENT DOCUMENTS 3,757,011  9/1973  Fleck .................................... 548/257
4,791,211  12/1988  Lund .................................... 548/257

FOREIGN PATENT DOCUMENTS 3334490  3/1984  Fed. Rep. of Germany ...... 548/257
2127407  2/1986  United Kingdom .

Primary Examiner—Donald G. Daus
Attorney, Agent, or Firm—Kevin T. Mansfield; Edward McC. Roberts

[57] ABSTRACT

2-(stilbyl-4″)-(naphtho-1′,2′:4,5)-1,2,3-triazole-2″-sulfonic acid is obtained by diazotizing p-aminostilbene sulfonic acid, coupling the resulting diazonium salt with Tobias acid and then oxidizing the resulting monoazo sodium salt to close the ring and form the naphthotriazolyl moiety, and, more particularly, by performing the ring-closure oxidation step in a solution of the monoazo compound in a mixture of 2-butoxyethanol and water with pressurized air by contacting said solution in the presence of a copper salt catalyst at temperatures in the range 105°–160° C. and at pressures in the range 10–80 psig, for a time sufficient to effect ring-closure.

7 Claims, No Drawings

MANUFACTURING PROCESS FOR A NAPHTHOTRIAZOLE STILBENE FLUORESCENT AGENT

This application is a continuation of application Ser. No. 259,506, filed Oct. 17, 1988, abandoned, which is a continuation of application Ser. No. 33,382, filed Apr. 2, 1987, now abandoned.

FIELD OF THE INVENTION

This invention relates to a stage in the manufacture of a hypochlorite-stable naphthotriazolyl stilbene fluorescent agent and more particularly to the forming of the triazolyl portion of the dye by conducting the ring-closure oxidation under pressure.

BACKGROUND OF THE INVENTION

The above-mentioned specific group of hypochloritestable naphthotriazolyl stilbene fluorescent whitening agents are described in U.S. Pat. No. 2,784,103, issued to Keller, Zweidler and Hausermann, on March 5, 1957. They were described as having an affinity to textile fibers, such as cellulose, polyamide, polyurethane, polyester and blends thereof. As this affinity occurs from aqueous solutions, they lend themselves to inclusion in powdered and liquid detergent compositions.

The preferred compound of this class is the sodium salt of 2-(stilbyl-4")-(naphtho-1',2':4,5)-1,2,3 triazole-2"-sulfonic acid.

The compound, marketed under the trademark Tinopal ® in large quantities, is manufactured by the following scheme:

Until this invention, the ring-closure step has been performed by air oxidation of the solution of the monoazo sodium salt in aqueous 2-butoxyethanol (Butyl Cellosolve), (BC), (Dowanol EB). The oxidation was performed by sparging air at atmospheric pressure through the aqueous solution of the monoazo salt in 2-butoxyethanol at the boiling point of the azeotrope of the solvent mixture (about 90°-95° C.). The reaction solution consisted of a 5-6 wt. % solution of the monoazo in an alkaline aqueous solution of 35 wt. % of 2-butoxy ethanol. It was carried out at the reflux of the azeotrope. A copper sulfate catalyst promoted the oxidation so that it could be completed within about 4-7 hours after initiating the air-sparging. After the oxidation was completed, as indicated by spot tests, the air-sparging was halted and $Na_2S_2O_4$, sodium hydrosulfate (sodium dithionite), was added to decompose trace amounts of colored impurities.

The physical properties of the reaction solvent, 2-butoxyethanol, hereinafter BC, and its mixtures with water have a great influence on the oxidative ring-closure of the monoazo to the triazole. Mixtures of this ether with water in the range between 5 and 75 wt. % of BC form a constant boiling azeotrope (b.p. 98.8° C.). This limits the maximum temperature available in the atmospheric oxidation process to 98.8° C.

During oxidation the triazole formed must remain in solution. If the triazole precipitates during the oxidation, solvent-containing red-colored by-products become trapped in the triazole crystals and the final product will be unacceptable. To prevent precipitation of the triazole, a minimum amount of BC (approximately 33 wt. %) has been required.

A. Diazotization

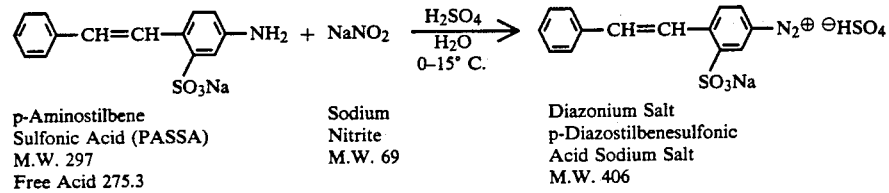

| p-Aminostilbene Sulfonic Acid (PASSA) M.W. 297 Free Acid 275.3 | Sodium Nitrite M.W. 69 | Diazonium Salt p-Diazostilbenesulfonic Acid Sodium Salt M.W. 406 |

B. Coupling

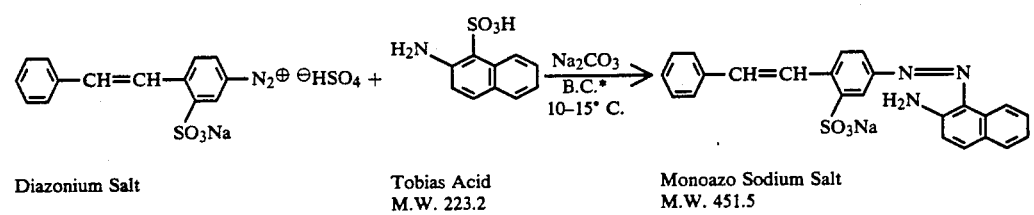

| Diazonium Salt | Tobias Acid M.W. 223.2 | Monoazo Sodium Salt M.W. 451.5 |

C. Oxidation

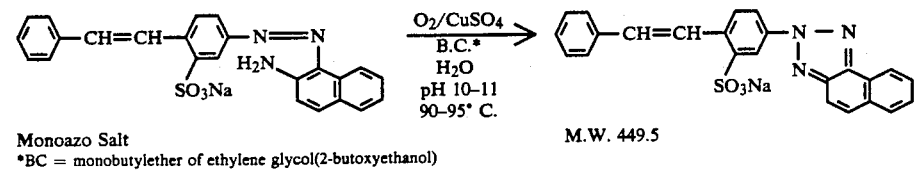

Monoazo Salt    M.W. 449.5

*BC = monobutylether of ethylene glycol(2-butoxyethanol)

The present invention is directed to step C, the oxidation step wherein the monoazo compound is converted to the final product by ring-closure of the monoazo intermediate to the triazole final product.

THE INVENTION

This invention is based upon the discovery that the triazole is soluble in mixtures of BC and water in which it was insoluble at the lower temperatures, particularly at the azeotrope boiling temperature, if the oxidation reaction were to be conducted at elevated temperatures by increasing the pressure during the oxidation.

The solubility of the triazole is increased to such an extent that the amount of BC for reaction medium can be considerably reduced. Also, as the reaction rate is increased by the elevated temperature and pressure, the oxidation of the monoazo to the triazole can be completed in about two hours as compared to the seven hours needed for the unpressurized reaction under reflux.

Thus, this invention consists of the steps of introducing the solution of 5-[N-(2'-amino)naphthyl]azo-2-(1'-phenyl)-ethenyl-benzene sulfonic acid, sodium salt in the concentration of up to 20% in about 15–50 (preferably about 30) wt. % aqueous solution of 2-butoxyethanol into a pressure vessel, adding a catalytic amount of a copper salt and then sparging into said pressure vessel, below the surface of the contained liquid, air, maintained at a pressure of about 20–40 psig and heating to 115°–140° C. (preferably about 125° C.) for 2–3 hours or a time sufficient to form the triazole compound from said monoazo. Said resultant triazole being the sodium salt of 2-(stilbyl-4")-(naphtho-1',2':4,5)-1, 2,3-triazole-2"-sulfonic acid.

Upon completion of the pressurized oxidation reaction, while the vessel is still pressurized, sufficient sodium dithionite is added to decolorize the mixture by destroying unwanted colored by-products.

DETAILED DESCRIPTION OF THE INVENTION

The synthesis of the naphthotriazolyl stilbene—subject of this invention—is based on the successive steps of diazotization, coupling and oxidation steps set forth in the reaction scheme (supra). The diazotization and coupling steps may be performed in batches or in a continuous reaction apparatus. These steps are merely ancillary to this invention. However, the oxidation step, since this reaction requires extended time, 4–7 hours at azeotropic distillation temperatures, or 2–3 hours at elevated pressure, is best performed in batch stages in suitably reinforced equipment. Parallel groups of reinforced vessels may be used to achieve throughput rates commensurate with the output of the previous stages and to meet the annual production requirements.

The pressurized air oxidation of this invention, closing the ring of the triazole from the monoazo compound, is operable from 10 to 80 pounds per square inch (psig), with 25 to 56 psig preferred and about 30 psig as regards materials handling, explosion hazards and purity of final product. At that pressure range, reaction temperatures of 105°–160° C. are possible with temperatures of 115°–150° C. usual at the preferred range and 120° C. at the optimum.

It has been determined that while a theoretical explosion hazard might exist during the oxidation step due to the possible flammability of the solvent vapors, analysis of the vented air with entrained solvent and water indicates that the vapors vented from the pressurized reactor were non-flammable.

The 2-butoxyethanol solvent (BC) can be recycled several times. The BC solvent can be steam-stripped after completion of the reaction followed by filtration of the desired product. Some of the BC can also be recovered from the condensers through which the vented reaction gas passes during the reaction period.

In the preferred isolation procedure the product is crystallized and filtered from the reaction mixture after removal of the BC by steam-stripping. After the BC is removed the product has very low solubility and there is nearly quantitative recovery on the filter. It is also possible to crystallize and filter the product without removing BC. In this case the filtrate containing BC and part of the product is recycled to the oxidation reaction to avoid product loss.

The desired naphthotriozolyl stilbene prepared by oxidation at elevated temperature is equal in quality to that produced by the previous process of atmospheric oxidation as measured by percent purity by absorption spectra and visual color.

In addition to the increased throughput of the intermediate monoazo compound, resulting from the more rapid completion of the reaction, an important direct benefit of operating at elevated pressure and temperature is the improved solubility of the product in the solvent, BC.

Consequently, the amount of BC required for the reaction is greatly reduced.

The solvent, BC, is lost to some extent in the oxidation stage, entrained and passing through the condenser with the air flow.

The major source of solvent loss, however, occurs in the product isolation stage.

Solvent losses are lower in the preferred method of isolation in which BC is removed by steam-stripping as an azeotrope with water prior to filtering the product. Unless the BC is removed to lower levels, however, the losses can still be significant. Reduction of BC content to only 2% would result in a loss of 33% of the BC initially charged. Reduction to 0.5% BC in the reaction mass is possible and this would reduce the BC loss to 8% of the initial charge.

It must be noted that stripping to lower BC content is achieved at the expense of energy cost for distilling the BC/water azeotrope and time. Both of these factors serve to cancel some of the economic gain by stripping to low BC levels.

The BC lost in the filtrate contributes to effluent in the process, requiring expensive treatment to prevent water pollution.

Some additional BC is lost in the condenser system by incomplete condensation of vapors but this is normally less than that lost in the filtrate.

By practicing this invention the amount of BC lost is significantly reduced. Since the amount of BC used in the oxidation reaction is only about half that required under normal, atmospheric oxidation conditions, less BC needs to be distilled and less time and energy are required to reduce it to low levels (0.5% or lower) by stripping. This provides a significant economic advantage while reducing water pollution.

In the direct filtration of product after cooling the reaction mass, an appreciable amount of BC solvent remains on the cake. This adherent solvent can be partially recovered by washing the cake with water but significant amounts remain. The BC losses using this procedure are normally larger than by the steam-stripping process and the BC contained in the water wash must be recovered by an additional distillation step.

If the direct filtration method of isolation is used the advantages of the pressure oxidation in which less BC is employed is even greater than when using the steam-stripping procedure. In each isolation method there is significant savings in solvent (amount used and recovered), energy, time and effluent.

The process will be described more fully in the examples. It is to be understood that the procedures are illustrative of the preferred mode but are merely exemplary. Changes in scale, art-recognized equivalent substitutes for the stated equipment and test devices are intended as long as they fall within the ambit of the current status of the art and within the metes and bounds of this disclosure of the invention.

EXAMPLE I

Laboratory Scale

A one-liter Parr reactor equipped with stirrer, reflux condenser equipped with pressure control valve, thermowell, pressure gauge, heating mantle, charging port and subsurface gas inlet with sparger is charged with 390 gm of the solution of 2-(stilbyl-4''-monoazo)-2-aminonaptho-2''-sulfonic acid sodium salt (0.125 mol-14.5% of the monoazo salt by HPLC assay) dissolved in 2-butoxyethanol (BC), 249 gm water, 10 gm of 50% NaOH and 0.5 gm $CuSO_4.5\ H_2O$.

The reactor is sealed and heated to 132°–135° C. with agitation. (The autogenous pressure is about 30 psig.)

The compressed air sparge is initiated and maintained at a moderate rate at 30 psig by controlling the pressure relief valve on the condenser. The air sparging is continued for 120 minutes. When the oxidation is completed, (TLC on samples) 20 gm of 10% aqueous solution of sodium hydrosulfite ($Na_2S_2O_4.2H_2O$) is introduced into the reaction mixture. The contents of the pressure vessel are cooled to 92°–94° C. and transferred under pressure to a two liter crystallizer. The reactor vessel is rinsed with two successive 300 gm portions of water. The rinse water portions are transferred to the crystallizer.

The product is then ready for isolation.

LAB ISOLATION

Stripping

Heat the oxidation mass to reflux and inject live steam to strip off the butyl cellosolve. The distillate separates into two layers, the lower water layer is returned to the distillation flash and the upper butyl cellosolve layer (55% BC) is removed. Adjust heating as required to keep the volume of the mixture constant. After the butyl cellosolve is removed as shown by a single layer in the distillate, the solid that precipitates is collected by suction filtration and washed on the filter with hot water (60° C.) until the filtrate is colorless. The light yellow crystals are dried overnight in a vacuum oven at 100° C. Purity of the product is 90–92% as shown by absorption spectra. Water and salt ($Na_2SO_4$) are the major impurities; only trace amounts of organic impurities are present.

Crystallization

Transfer reaction mass and wash to a three liter reactor equipped with a mechanical stirrer. Cool slowly to 50° C. then add 1500 gm $H_2O$. Cool to <10° C. and filter out product. Wash product with $H_2O$ until the filtrate is clear. Dry overnight in a vacuum oven at 70° C.

EXAMPLE II

Pressure Oxidation on Plant Scale

Charge a 3000 gallon stainless steel oxidation kettle with 9800 lbs of the monoazo solution containing 1400 pounds of monoazo (as 100%) and 4650 pounds of 2-butoxyethanol (as 100%) and balance water. To this charge add 750 gallons of water and 40 gallons of 50% NaOH (in water). 12 pounds of copper sulfate crystals are then added to the contents. The contents are about 2000 gallons. The pH must be 12–13.

The kettle is sealed, agitation is started and the contents are sparged with compressed air vented through a pressure relief valve set at 30 psig, while heating the vessel contents to 120° C. The compressed air flow is maintained at 30 psig/20–30 cfm (53–63 scfm)/120° C. for two hours. The pH at the completion of the reaction must be >11. The completion of the oxidation reaction is followed by TLC. When the reaction is found to be complete, add to the kettle under pressure, 60 gallons of 10% aqueous solution of sodium hydrosulfite and hold for 20 minutes with agitation. Charge 150 gallons of water at room temperature to the vessel contents and allow the vessel to cool to 95° C. Vent the kettle slowly to atmospheric pressure and transfer contents to a 5000 gallon stainless steel stripping kettle equipped with a water-cooled condenser to a decanter.

Rinse the reaction vessel with portions of water. The total rinse water should be about 1600 gallons. This rinse amount is necessary to provide the correct product slurry for solvent stripping. The contents in the stripping kettle consists of about 3800 gallons of slurry containing about 1600 pounds of the naphthotriazole stilbene product and 4675 pounds of 2-butoxyethanol (as 100%).

Agitation is started in the stripping kettle and the vent is opened to the condenser. The contents are heated to 99°–100° C. and when distillation starts, a steam sparge into the kettle is started. The condensate is run into a decanter where the condensate (50°–70° C.) splits into two phases. The upper 2-butoxyethanol-rich phase (54% BC) is transferred to storage for recycling and the lower, water-rich phase (10% BC) is returned to the stripping kettle through the packed section of the vapor column. The steam sparge rate is adjusted so that one pound of steam is added to the kettle for each pound of BC-rich phase that is transferred to storage. The volume within the stripping kettle should preferably be maintained constant.

The distillation is complete when the BC content in the stripping kettle is <0.5 wt. % BC. When the distillation is complete, the contents of the stripping kettle are cooled to about 90° C. and the resulting slurry is pumped to the filter.

The yield is about 5300 lbs of wet cake containing 1550 pounds of the sodium salt of 2-(stilbyl-4'')-naphtho-1',2':4,5)-1, 2,3-triazole-2''-sulfonic acid.

The yield, based on the monoazo salt is about 95–98%.

The purity is equal to or better than the product obtained by oxidation with atmospheric air.

What is claimed is:

1. In a process for preparing 2-(stilbyl-4'')-(naphtho-1',2':4,5) -1,2,3-triazole-2''-sulfonic acid which involves the steps of diazotizing p-aminostilbene sulfonic acid, coupling the resulting diazonium salt with Tobias acid and then oxidizing the resulting monoazo sodium salt with air in a mixture of 2-butoxyethanol and water in the presence of a copper salt catalyst for a time sufficient to effect ring-closure, wherein the improvement comprises performing the ring-closure oxidation step with pressurized air at temperatures in the range of 105°–160° C. and at pressures in the range of 10–80 psig and in a reaction mixture which contains from 15 to 50 weight percent of 2-butoxyethanol.

2. In the process according to claim 1 wherein said oxidation is performed at temperatures of 110° to 150° C. and at the autogenous pressures thus generated.

3. In the process according to claim 1 wherein said oxidation is performed at about 120° C. and 30 psig.

4. In the process according to claim 1 wherein said catalyst is copper sulfate.

5. The process according to claim 1 wherein said 2-butoxyethanol comprises about 30% of said oxidation reaction solution.

6. The process according to claim 1 wherein after said ring closure by pressurized air, the oxidizing reaction is halted by the addition to said solution of a sufficient amount of sodium hydrosulfite ($Na_2S_2O_4 \cdot 2H_2O$).

7. The process according to claim 1 wherein said contacting of said solution with pressurized air is continued for between 2 to 3 hours at 125° C. and about 2 atmospheres until said ring closure is completed.

* * * * *